United States Patent [19]
Michaels

[11] Patent Number: 6,086,853
[45] Date of Patent: Jul. 11, 2000

[54] MEDICATED VAPOR CANDLE

[76] Inventor: Robert S. Michaels, 3196 Stevenson Rd., Anger, N.C. 27501

[21] Appl. No.: 09/237,593

[22] Filed: Jan. 25, 1999

[51] Int. Cl.[7] .................................................. A01N 25/08
[52] U.S. Cl. ........................... 424/40; 424/76.1; 424/76.2
[58] Field of Search ................... 424/40, 195.1, 424/DIG. 5, 76.1, 76.2

[56] References Cited

U.S. PATENT DOCUMENTS

| | | |
|---|---|---|
| 21,706 | 10/1858 | Tatum . |
| 748,511 | 12/1903 | Liebreich . |
| 1,519,053 | 12/1924 | Rew . |
| 1,672,463 | 6/1928 | Morczewski . |
| 2,003,684 | 6/1935 | Frantz . |
| 2,323,804 | 7/1943 | Driscoll . |
| 2,465,474 | 3/1949 | Peterson . |
| 3,175,876 | 3/1965 | Fredericks . |
| 3,898,039 | 8/1975 | Lin . |
| 4,427,366 | 1/1984 | Moore . |
| 4,568,270 | 2/1986 | Marcus et al. . |
| 5,876,706 | 3/1999 | Zaunbrecher ........................ 424/76.1 |

Primary Examiner—Thurman K. Page
Assistant Examiner—R. Bawa
Attorney, Agent, or Firm—Mills Law Firm PLLC

[57] ABSTRACT

This invention is a composition of matter and method of preparing the same. More specifically the present invention is a medicated vapor candle consisting of a homogenous mixture having approximately three parts petroleum jelly containing the active ingredients of camphor, menthol and eucalyptus, melted and mixed with four parts candle wax. The active ingredients, by volume, of approximately 5% camphor, 2.5% menthol and 1.2% eucalyptus oil.

9 Claims, 1 Drawing Sheet

MEDICATED VAPOR CANDLE

FIELD OF THE INVENTION

This invention relates to candles, and more particularly to candles that, when ignited, gives off a controlled release of medicated constituent into the atmosphere.

BACKGROUND OF INVENTION

Candles have for centuries been used to provide light. Over the years other ingredients have been added to give fragrances to candles, to repel insects and even claims of medicated combustibles.

Some of the problems encountered in using these products is a lingering odor after the candle or other combustible has been extinguished. Also the fragrances can be quite strong while burning and are extremely irritating to many people.

CONCISE EXPLANATION OF REFERENCES

U.S. Pat. No. 3,898,039 to Tong Joe Lin entitled Fumigant Container Substrate for Diffusion Promoting Candle is a candle that has a substrate bearing fumigant. The fumigant diffuses when exposed to the thermal energy of a candle. The fumigant substrate in combination with a candle is usable as a fragrance candle and also be useful to relieve the symptoms of a cold.

U.S. Pat. No. 1,519,053 to John Edmond Rew entitled Medicated Combustible is stated to have therapeutic value in the treatment of toothache, bronchitis, colds, asthma, palpitation of the heart, headache, hay fever, and the like. The primary ingredients include ginger, charcoal and nutmeg.

U.S. Pat. No. 21,706 to Joel H. Tatum entitled Manufacture of Candles uses inferior materials such as ordinary candle stock, and combines good tallow, gum camphor, white rosin or wax and gum dammar to create the product.

U.S. Pat. No. 2,323,804 to Phillip J. Driscoll entitled Citronella Candle uses a compound of paraffin and citronella oil to repel mosquitoes.

U.S. Pat. No. 4,568,270 to Marcus, et al, assigned to Ortiz, Inc. entitled Biconstituent Candle combines a mixture of paraffin, wax and a fragrance oil in the core which constitute 5 to 12% of the total weight of the core.

U.S. Pat. No. 3,175,876 to William M. Fredericks entitled Scent Producing Candle and Method for Making Same includes pungent spicy scents such as cinnamon oil, rose oil and the like.

U.S. Pat. No. 1,672,463 to John Morczewski, one third interest assigned to Andrew A. Kekko entitled Candle provides for an improved combustion using oil of wintergreen, kerosense, aqua ammonia, glycerine, banana oil and paraffin.

U.S. Pat. No. 748,511 to Oscar Liebreich entitled Fat-Like Substance and Process of Making Same discloses an admixture containing fat like substances to provide an improved product.

U.S. Pat. No. 2,003,684 to Emile Frantz entitled Incense uses a slowly combustible material consisting of the ground parts of the eucalyptus tree molded into a form.

U.S. Pat. No. 2,465,474 to Dell R. Peterson entitled Fragrance Emitting Device uses perfume or the like to give off a pleasant odor without requiring perfume to be incorporated within the tallow of the candle.

Finally, U.S. Pat. No. 4,427,366 to Kenneth L. Moore entitled Scented Candle discloses a scented candle surrounded by odorizing chips.

BRIEF DESCRIPTION OF INVENTION

After much research and study into the above mentioned problems, the present invention has been developed to provide a candle that, when burning, gives off a controlled release of medicated constituent into the atmosphere, relieves nasal congestion associated with the common cold and controls antitussive activity. This translates into the symptomatic relief of nasal congestion, bronchial mucus congestion, coughs due to colds.

The above is accomplished by combining the active ingredients camphor, menthol and eucalyptus in a petroleum base such as petroleum jelly with paraffin to form either a container candle or a free standing candle from a candle mold.

In addition to the above, the medicated vapor candle of the present inventions leaves no residual ambient odors once it has been extinguished. In other words so long as a candle is burning it gives relief as described above, but once the candle has been extinguished, it ceases releasing medicated vapor and the air clears with no residual scent.

In view of the above, it is an object of the present invention to provide a medicated vapor candle that, when ignited, relieves nasal congestion associated with the common cold.

Another object of the present invention is to provide a medicated vapor candle that, when ignited, controls antitussive activity.

Another object of the present invention is to provide a medicated vapor candle that, when ignited, relieves nasal congestion when associated with the common cold and controls antitussive activity.

Another object of the present invention is to provide a vapor candle that, when ignited, gives symptomatic relief of nasal congestion, bronchial mucus congestion, coughs due to colds and muscular soreness due to colds.

Another object of the present invention is to provide a candle that contains camphor, menthol and eucalyptus oil in a petroleum base that is mixed with paraffin to give off a medicated vapor when ignited.

Another object of the present invention is to provide a candle that, when ignited, emits medicated vapor resembling the vapor emitted from mitigated vapor rubs.

Another object of the present invention is to provide a relatively inexpensive and yet highly effective medicated vapor candle.

Other objects and advantages of the present invention will become apparent and obvious from a study of the following description and the accompanying drawings are illustrations of such invention.

DETAILED DESCRIPTION OF INVENTION

Figure 1:
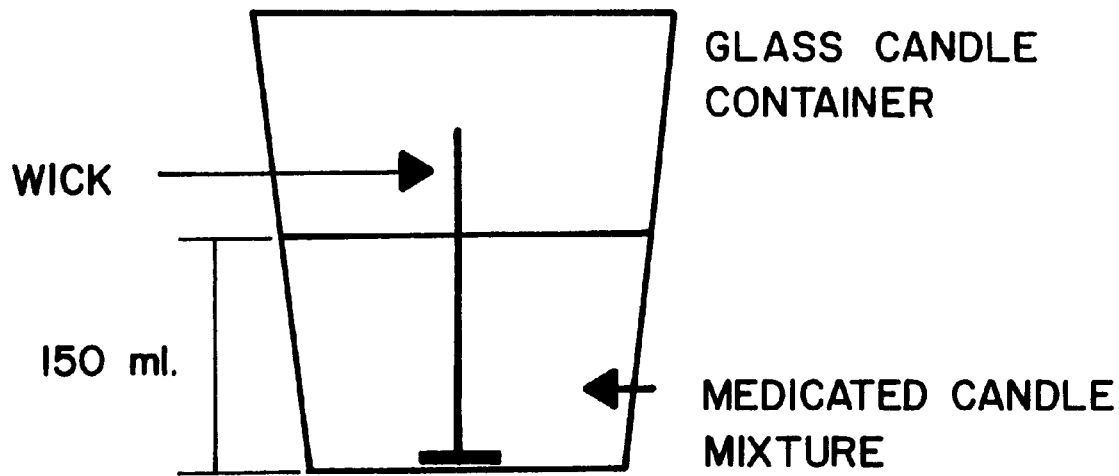
FIG. 1 is a somewhat schematic representation of the medicated vapor candle of the present invention in a glass candle container.
Figure 2:
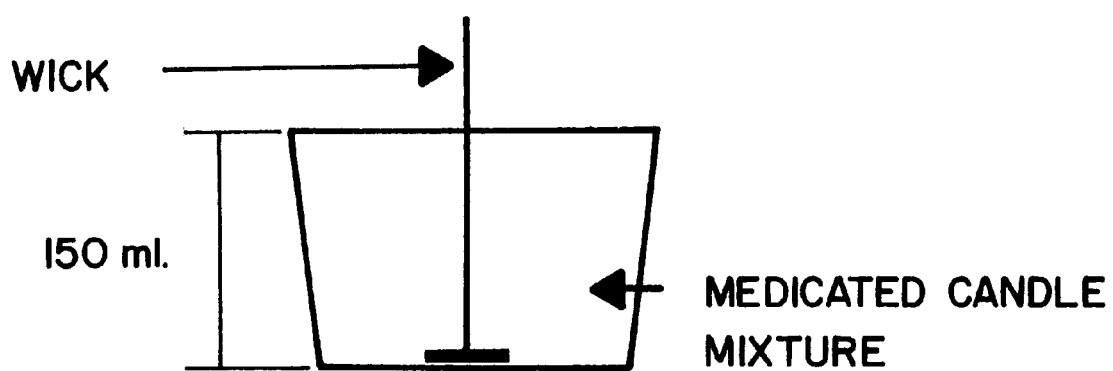
FIG. 2 is a somewhat schematic representation of a molded candle.

The medicated vapor candle of the present invention is three parts by volume vapor rub and four parts by volume paraffin wax, candle tallow, or other suitable candle base.

The vapor rub includes the active ingredients of 4.8% camphor, by volume, 2.6% menthol, by volume, 1.2% eucalyptus oil, by volume, and plus petroleum jelly.

An example of a vapor rub satisfactory for use in the medicated vapor candle in the present invention is Vicks® Vapor Rub manufactured by Proctor & Gamble of Cincinnati, Ohio.

A paraffin wax that has been found suitable for use in the medicated vapor candle of the present invention is Gulf Household Wax distributed by Lite & Wizard Distributing of Memphis, Tenn.

A 2", 15 mm #2 wick with a base or clip has been found to work well when in a candle glass or candle mold with the heated mixed ingredients being poured to a depth of 150 ml.

The medicated vapor candle of the present invention is made by combining three parts of petroleum jelly containing the active ingredients of camphor, menthol and eucalyptus with four parts melted paraffin wax and blending the same to a homogenous mixture. This melted mixture is then poured into either the candle glasses or candle molds and allowed to cool to form the medicated vapor candle of the present invention.

When the medicated vapor candle of the present invention is ignited, vapor rub vapors are emitted giving the same benefits as vapor rub but without the mess created by the petroleum jelly component. The candle burns cleanly and only emits medicated vapor while ignited.

The present invention may, of course, be carried out in other specific ways than those herein set forth without departing from the spirit and essential characteristics of such invention. The present embodiments are, therefore, to be considered in all respects illustrations and not restrictive, and all changes coming within the meaning and equivalency range of the appended claims are intended to be embraced therein.

What is claimed is:

1. The method of making a candle that gives off a controlled release of medicated constituent when burned comprising:

melting candle wax;

blending the melted candle wax with a petroleum jelly base having active ingredients of camphor, menthol and eucalyptus to form a homogeneous mixture; and forming a candle having a wick from the homogeneous mixture whereby when the candles are burned, they emit medicated constituent into the atmosphere.

2. The method of claim 1 wherein the petroleum jelly base is approximately three parts, by volume, and the candle wax is approximately four parts, by volume.

3. The method of claim 1 wherein the active ingredients in the petroleum jelly base is, by volume, approximately 5% camphor, 2½% menthol and 1% eucalyptus oil.

4. A medicated vapor candle comprising: a candle body and a wick, said candle body comprising a homogeneous mixture of candle wax and petroleum jelly wherein said petroleum jelly contains as vaporizable constituents a mixture of camphor, menthol and eucalyptus.

5. The medicated vapor candle as recited in claim 4 wherein said candle wax is paraffin wax.

6. The medicated vapor candle as recited in claim 4 wherein said candle wax is candle tallow.

7. The medicated vapor candle as recited in claim 4 wherein said candle body comprises about three parts petroleum jelly and about four parts candle wax.

8. The medicated vapor candle as recited in claim 7 wherein said vaporizable constituent comprise by volume of petroleum jelly about 5% camphor, 2.5% menthol, and 1% eucalyptus.

9. A medicated vapor candle comprising: a homogeneous mixture of medicated petroleum jelly and candle wax, and a candle wick carried in said homogeneous mixture, said homogeneous mixture comprising about three parts medicated petroleum jelly and four parts candle wax, said medicated petroleum jelly containing a mixture of camphor, menthol and eucalyptus oil as vaporizable constituents in an amount by volume of about 4.6% camphor. 2.6% menthol, and 1.2% eucalyptus oil.

* * * * *